(12) United States Patent
Wilbur

(10) Patent No.: US 7,654,149 B2
(45) Date of Patent: Feb. 2, 2010

(54) ROLLER CHAIN WEAR GAUGE

(75) Inventor: John Richard Wilbur, Bettendorf, IA (US)

(73) Assignee: Drives, LLC, Fulton, IL (US)

( * ) Notice: Subject to any disclaimer, the term of this patent is extended or adjusted under 35 U.S.C. 154(b) by 0 days.

(21) Appl. No.: 12/025,553

(22) Filed: Feb. 4, 2008

(65) Prior Publication Data
US 2009/0193907 A1  Aug. 6, 2009

(51) Int. Cl.
*G01N 3/08* (2006.01)
(52) U.S. Cl. ........................................... 73/829
(58) Field of Classification Search .................. 73/828, 73/829; 33/501.7, 567
See application file for complete search history.

(56) References Cited

U.S. PATENT DOCUMENTS

| | | | | |
|---|---|---|---|---|
| 69,954 | A | * | 10/1867 | Richards ................... 33/544.4 |
| 386,469 | A | * | 7/1888 | Howard ........................ 33/806 |
| 450,065 | A | * | 4/1891 | Fontaine ..................... 33/704 |
| 3,417,475 | A | * | 12/1968 | Vlasaty ....................... 33/502 |
| D229,222 | S | * | 11/1973 | Paulk .......................... D10/64 |
| D243,232 | S | * | 2/1977 | Kuenzig ...................... D10/73 |
| 4,150,488 | A | * | 4/1979 | Behnke ........................ 33/567 |
| 4,365,420 | A | | 12/1982 | Walden |
| 4,888,876 | A | | 12/1989 | Meredith et al. |
| 5,199,180 | A | | 4/1993 | Yablonsky |
| 6,178,824 | B1 | | 1/2001 | Hayakawa et al. |
| 6,748,667 | B2 | * | 6/2004 | Sevastian .................. 33/501.45 |
| 7,040,151 | B2 | * | 5/2006 | Graham et al. ................. 73/121 |
| 7,188,430 | B2 | * | 3/2007 | Tange ......................... 33/544.4 |

OTHER PUBLICATIONS

British Standard Roller Chain specifics, p. 26, Renold Jeffrey Roller Chain Catalog, http://www.renoldjeffrey.com.
Rohloff Caliber 2 Product Information, © 2004, Rohloff AG, http://www.rohloff.de/fileadmin/rohloffde/download/beschreibung/caliber2/beschreibung_caliber_2.en.pdf.
Brandt, Jobst, Chain Wear Measuring Tools, Jan. 2004, http://www.pardo.net/bike/pic/fail-004/000.html.
Brown, Sheldon, Chain Maintentnace, © 2007, http://www.sheldonbrown.com/chains.html.
Park CC-3 Chain Checker at JensonUSA.com, © 2007, http://www.jensonusa.com/store/product/TL605A00-Park+Cc-3+Chain+Checker.aspx.

(Continued)

*Primary Examiner*—Lisa M Caputo
*Assistant Examiner*—Freddie Kirkland, III
(74) *Attorney, Agent, or Firm*—Vedder Price, P.C.

(57) ABSTRACT

The present disclosure relates to a handheld, single-piece wear gauge for chains, and more specifically, to a wear gauge with an elongated body carved into segments with markings, varied widths, and varied heights arranged along a guiding back rail. A roller chain wear gauge includes a single-piece body with a measuring end and a handle connected to the measuring end, wherein the measuring end includes a plurality of adjacent and contiguous calibrated segments each having a measuring length, a measuring width, and a measurement marking, and wherein the measuring end defines on one side a back rail formed by an alignment of a first side of each of the calibrated segments and a step function formed by the second side of each of the calibrated segments.

10 Claims, 5 Drawing Sheets

OTHER PUBLICATIONS

Rohloff Caliber 2 Technical Specification, Rohloff AG, http://www.rohloff.de/en/products/caliber_2/.

International Searching Authority, Search Report for PCT/US2009/031531, Mar. 11, 2009, United States.

Roller Chain. Wikipedia: The Free Encyclopedia [online]. FL: Wikimedia Foundation, Inc. Jan. 14, 2008 [retrieved on Feb. 23, 2009]. Retrieved from the internet: <URL: http://en.wikipedia.org/w/index.php?title=Roller_chain&diff=184198614&oldid=179605088>; "Wear" section; "Variants in Design" section.

* cited by examiner

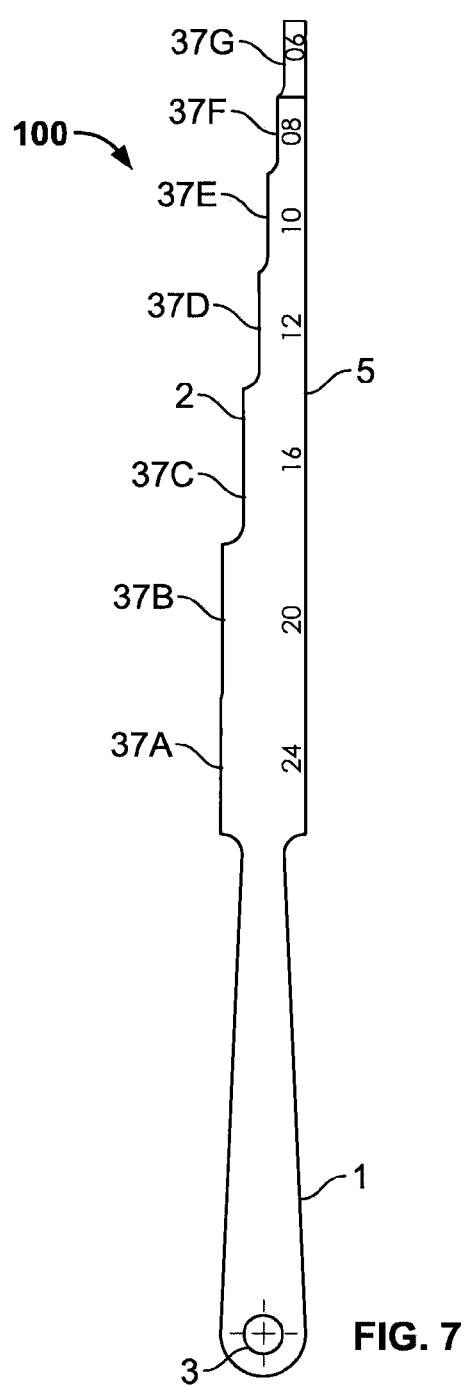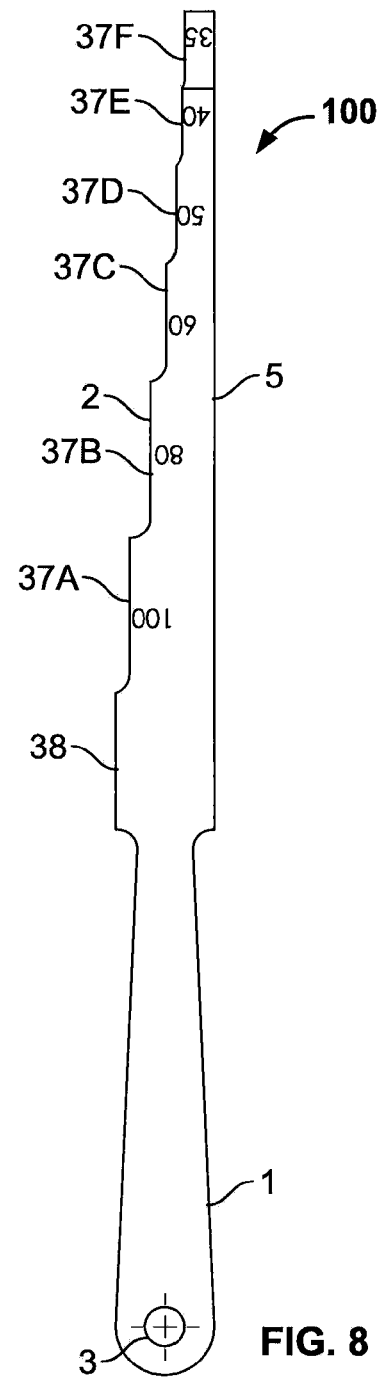
FIG. 7
FIG. 8

ROLLER CHAIN WEAR GAUGE

FIELD OF THE DISCLOSURE

The present disclosure relates to a handheld wear gauge for chains, and more specifically, to a wear gauge with an elongated, single-piece body capable of measuring multiple sizes of roller chains without need for dismounting the chain.

DEFINITIONS

Within the scope of this disclosure, the word "chain" or "chains" is defined as any material such as chain, cable, line, thread, wire, tape, yarn, jewelry, or any other flexible, longitudinal material capable of being stored on a spool or any variation thereof. The term "industrial chain" is defined as a subset of the chains defined above made of industrially sized metallic chains used in the mechanical industry such as a roller chain or ball chain. A "roller chain" is defined as a series of alternating internal and external links, the external links made with pins pressed to outer plates and the internal links made of bushings pressed onto inner plates, wherein each pin of an external link is connected to rotate within an adjacent bushing of an internal link.

BACKGROUND

Roller chains are used to transfer force from one rotating axle to an adjacent rotating axle. On a bicycle, a cyclist pushes pedals in a circular motion to rotate a center sprocket where a first portion of a roller chain is mounted. The second portion of the roller chain is mounted on a second sprocket mounted on the back wheel of the bicycle. As the first sprocket rotates, one portion of the chain, generally the top portion, is placed under strain and transfers the applied rotational force to the second sprocket and ultimately the back wheel. Roller chains in the mechanical industry work under the same principle. Chains can be reinforced by using larger links or by adding serial chains mounted on serial sprockets mounted on a drive axle.

Each link of a roller chain is placed cyclically under strain in one portion of the entire chain and released in the other portions of the chain. For example, in bicycles, the top portion of the chain is under strain while the bottom portion is free to hang under its own weight. As a result of this cyclical load, chains can be damaged by grinding wear. To minimize wear, friction must be reduced using use lubricants, rollers in or around the pins, or other systems such as intermediate sprockets to better distribute strain. Wear is any undesirable permanent mechanical degradation and ultimately leads a loss in efficiency and breakage. The measurement of wear in a roller chain is desirable to prevent breakage and to monitor and calibrate strain placed on chains.

Since roller chains are most often found with external links with two end pins and internal links end bushings inserted around the end pin of an external link, friction occurs mainly at the bushing/pin area. In a first type of wear, the pin is slowly damaged and its external radius is reduced. In a second type of wear, the bushing is slowly damaged and its internal radius is also reduced. In both of these instances of mechanical wear, the distance between two pins on the same external link remains unchanged, and the distance between two bushing on the same internal link also remains unchanged. The distance between adjacent external links and adjacent internal links increases gradually as wear increases in the bushing/pin area.

As the roller chain wears out, it becomes longer. Known methods in the art to measure wear include removing the chain from the sprockets to measure of a fixed length of chain with a ruler. This method has the obvious disadvantage of being imprecise and requires removing the chain from its operating position, which can be an extremely messy procedure, and having documented the original lengths of chain before wear occurs. Unworn chains with loose rollers can offset a ruler wear measurement.

Another technology used to measure wear is shown in U.S. Pat. No. 6,178,824 or in the marketplace as the Rohloff™ Caliber 2 or the Pack™ CC-3 Chain Checker. These devices are go/no-go gauges where one part of the tool is inserted around a first bushing at a heel and the tool is then rotated down. If the link is worn, a toe slides next to an adjacent bushing. These gauges are impractical to use, they are not adjusted for different sizes or models of chains, the tool to be slid in the chain opening cannot be located next to obstacles, and handles can obstruct measurement. These devices, due to their complex geometries, also are more prone to measurement error by unqualified operators. If the heel is not slid properly into position before the measurement is taken, the toe cannot "go" in a link, which results in a false negative.

Another technology is shown in U.S. Pat. Nos. 5,199,180 and 4,888,876 as long cylindrical or triangular telescoping sticks that are dropped inside the chain to measure wear. These multisectional devices also suffer inherent problems. First, wear gauge tools may need to be held in difficult orientations and positions to test the roller chains. For this reason, the telescoping system opened by gravity cannot measure from the underside of a chain. Gauges must also be as light as possible to obtain an unambiguous reading. The use of large handles or thick gauges is also problematic. In the case of telescopic gauges, if any of the segments of the gauge is partly unlocked, the operator obtains a false positive when the tip of the gauge does not slide into the chain but gives the impression of movement by retracting within the handle.

What is needed simple, light gauge capable of measuring wear of different sizes of roller chain with no chance of having false positive or negative measurements due to the operation of the gauge measuring a chain in any orientation or configuration.

SUMMARY

The present disclosure relates to a handheld, single-piece wear gauge for chains, and more specifically, to a wear gauge with an elongated body carved into segments with markings, varied widths, and varied heights arranged along a guiding back rail. A roller chain wear gauge includes a single-piece body with a measuring end and a handle connected to the measuring end, wherein the measuring end includes a plurality of adjacent and contiguous calibrated segments each having a measuring length, a measuring width, and a measurement marking, and wherein the measuring end defines on one side a back rail formed by an alignment of a first side of each of the calibrated segments and a step function formed by the second side of each of the calibrated segments.

BRIEF DESCRIPTION OF THE DRAWINGS

Certain embodiments are shown in the drawings. However, it is understood that the present disclosure is not limited to the arrangements and instrumentality shown in the attached drawings, wherein:

FIG. 7 is a front view of another embodiment of the roller chain wear gauge of FIG. 1 for measure of 06 to 20 size chains under British Standard.

FIG. 8 is a front view of yet another embodiment of the roller chain wear gauge of FIG. 1 for measure of 35 to 100 size chains under the ANSI Standard.

DETAILED DESCRIPTION

The present invention is not limited to the particular details of the device depicted, and other modifications and applications may be contemplated. Further changes may be made in the device described herein without departing from the true spirit of the scope of the disclosure. It is intended, therefore, that the subject matter of the above depictions should be interpreted as illustrative, not in a limiting sense.

Figure 1:
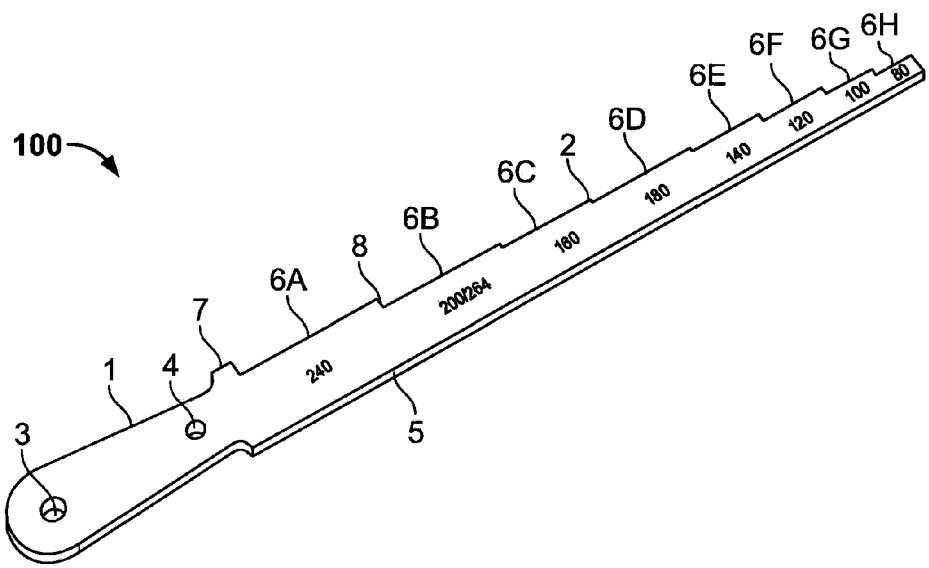
FIG. 1 is a perspective view of the roller chain wear gauge according to a first embodiment of the present disclosure.
Figure 2:
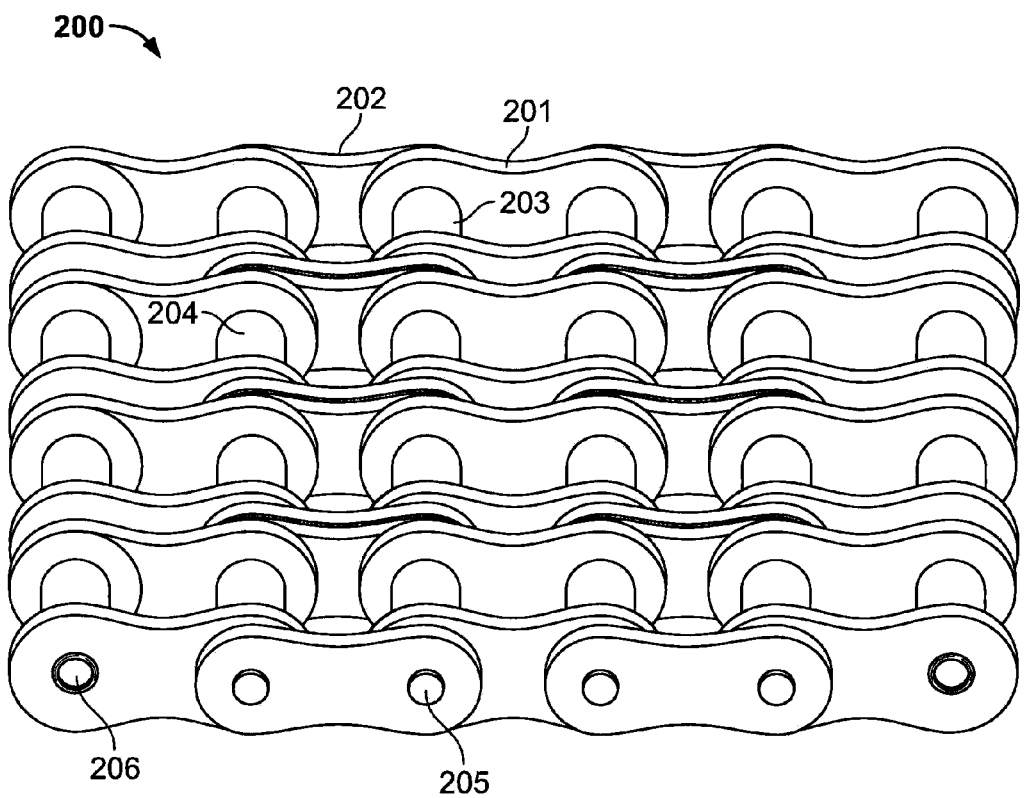
FIG. 2 is a side view of a multistand roller chain illustrating the different components of a typical roller chain according to another embodiment of the present disclosure.

FIG. 1 is a perspective view of the roller chain wear gauge 100 according to an embodiment of the present disclosure. While a roller chain wear gauge is shown and disclosed hereafter, what is contemplated is the use of the disclosed embodiment and technology associated with a chain wear gauge used with any type of chain as long as wear can be measured by determining the increased distance measured between the different links of the chain. In one embodiment, the roller chain wear gauge 100 includes a single-piece body with a measuring end 2 and a handle 1 connected to the measuring end 2. In the embodiment as shown, the handle 1 includes a grip 71 and circular openings 3, 4 to secure the gauge 100 to any surface using an attachment means, such as a hook to a wall or within a tool cabinet (not shown). The handle 3 includes a rounded palm and an edge 72 to define the end of the rail 5 and a stop 7 to prevent a user from testing a chain larger than what can be measured by the gauge shown in FIG. 1 as 240 from lowering the handle 1 between the different links of a chain to be measured 200 as shown in FIG. 2. What is shown in FIG. 1 is a wear gauge 100 cut from a thin sheet of stainless steel material made of pre-hardened steel. What is also contemplated is the use of a handle 1 of thickness different from the measuring end 2.

The wear gauge 100 includes a measuring end 2 with a plurality of adjacent and contiguous calibrated segments shown in 6A, 6B, . . . 6H. Each of these segments has a measuring length and thickness of at least the thickness of a chain to be controlled. Roller chains as shown in FIG. 1 are described using the ANSI standard where the last digit used is a 0 for standard chain, a 1 for lightweight chain, and 5 for bushed chain with no roller. The first digit(s) indicate the pitch of the chain (or the distance between two pins) in eighths of an inch. In FIG. 1, what is shown is a gauge 100 with successive segments 6A, 6B, . . . 6G having a marking of 240, 200/264, 160, 180, 140, 120, 100, and 80 respectively corresponding to standard chains of 3, 2½, 2, 2¼, 1¾, 1½, 1¼, and 1 inch in pitch, respectively. What is shown as FIG. 7 is a chain wear gauge 100 where each of the segments 37A, 37B, . . . 37G is calibrated based on the British Standards to accommodate chains having a marking of 24, 20, 16, 12, 10, 8, and 6 respectively corresponding to standard chains with a pitch of 1½, 1¼, 1, ¾, ⅝, ½, and ⅜ inch in pitch, respectively. FIG. 8 is a chain wear gauge 100 where each of the segments 39A, 39B, . . . 39F includes markings of 100, 80, 60, 50, 40, and 35 corresponding to standard chains with 1¼, 1, ¾, ⅝, ½, and ⅜ for bushed chains in inches respectively. Each of these three models of chain wear gauges 100 are directed to several possible embodiments of the present disclosure.

Figure 3:
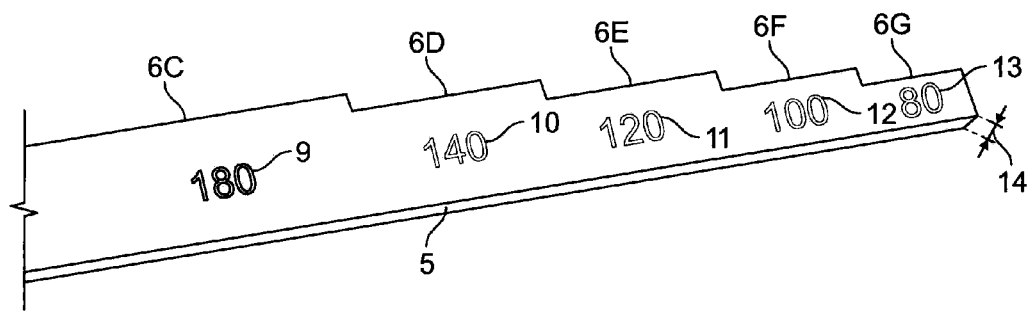
FIG. 3 is a close-up perspective view of the measuring portion of roller chain wear gauge of FIG. 1 according to a possible embodiment of the present disclosure.

In one embodiment, a 0.188 inch thick plate is used through the gauge with the smallest segment having a thickness of only 0.173 inch. For larger gauges, such as shown in FIG. 1, the gauge 100 has a general thickness of 0.25 inch. Each segment 6A-H as shown on FIG. 1 includes a measuring width shown in FIG. 5 as 30-35, and includes a measurement marking 9-13 as shown in FIG. 3. As way of a typical embodiment, the width of each segment each with a tolerance of +0.002 inch and −0.000 inch is given here below:

| Segment | FIG. 1 Gauge | FIG. 7 Gauge | FIG. 8 Gauge |
| --- | --- | --- | --- |
| A | 1.217 | 0.545 | 0.540 |
| B | 1.015 | 0.537 | 0.403 |
| C | 0.940 | 0.405 | 0.304 |
| D | 0.915 | 0.297 | 0.244 |
| E | 0.808 | 0.244 | 0.203 |
| F | 0.672 | 0.180 | 0.186 |
| G | 0.540 | 0.136 | |
| H | 0.403 | | |

While standard flat chains are shown, what is contemplated is the use of any type and geometry of chain. What is also not shown is the use of a connecting link to close the roller chain in a closed loop configuration using a pin held by a C-clip, a friction fit pin, an offset link, or a spring clip connecting link. As shown, most roller chains are made of plain carbon or alloy steel, but stainless steel is also contemplated in other types of applications where lubrication may be a problem.

Figure 5:
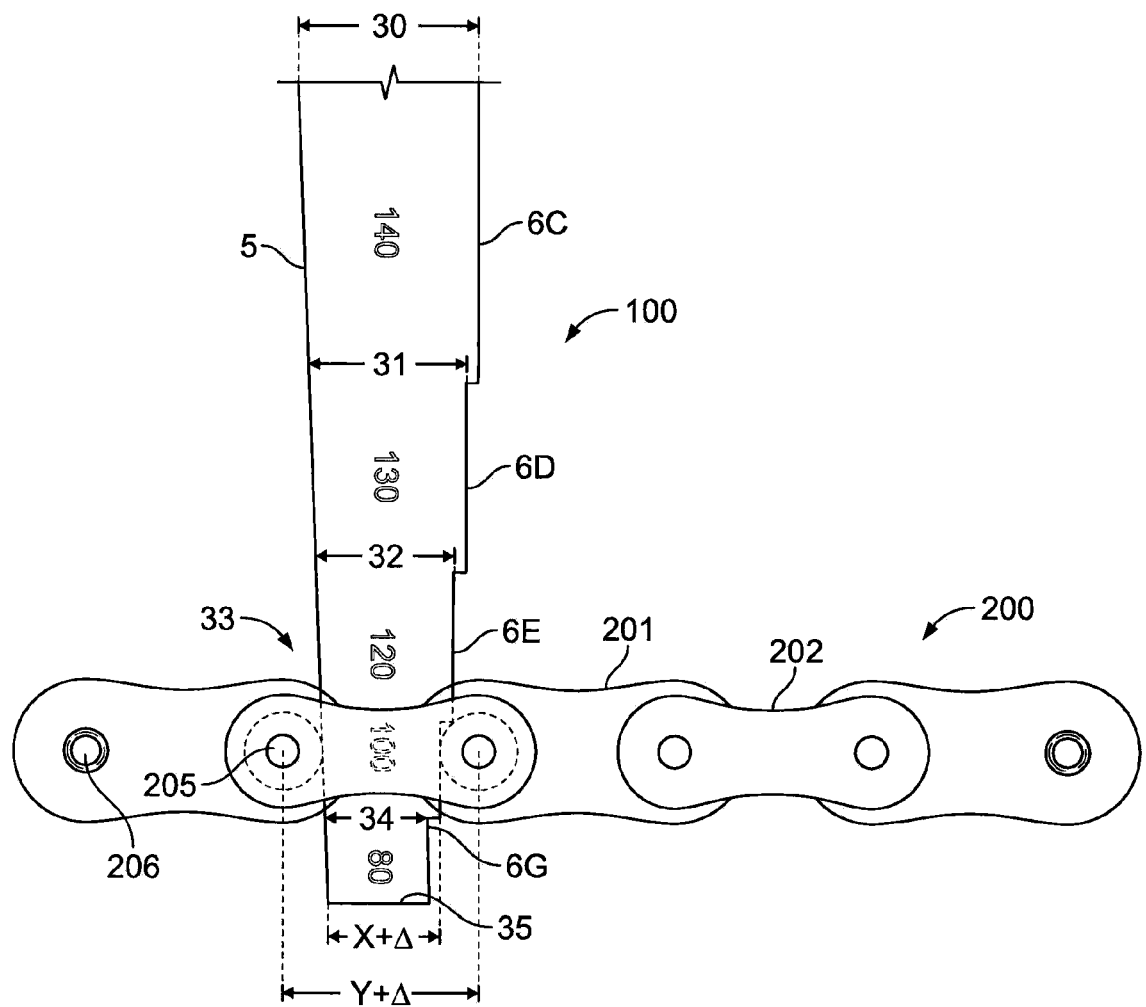
FIG. 5 is a functional side view of the measure portion of the roller chain wear gauge of FIG. 1 inserted between two adjacent links of the multistand roller chain of FIG. 4 according to an embodiment of the present disclosure.

In a preferred embodiment, the measurement markings are placed in the middle portion of the segments 6A-H so as to hide the measurement between the external link side plates 202. Returning to FIG. 1, the measuring end 2 defines on one side of the body of the gauge 100 a back rail 5 formed by an alignment of a first side of each of the calibrated segments 6A-H, and on the opposite side a step function formed by the second side of each of the calibrated segments 6A-H. By placing the different calibrated segments 6A-H in a step function, the segment with the smallest width 6H is located in the position farthest from the handle 1. The gauge 100 can be used for a plurality of different roller chain 200 sizes as shown when smaller segments are passed through the testing area to reach subsequent segments, such as 6F. As shown in FIG. 5, for example, if a #100 chain must be gauged, the user inserts the first segment 6H designed to test #80 roller chains through the opening to be measured between adjacent links until the step function of segment 6F reaches the outer roller 203. The measure markings 9-13 on each of the calibrated segments 6A-H is a size of the chain to be gauged by the marked segment.

Figure 4:
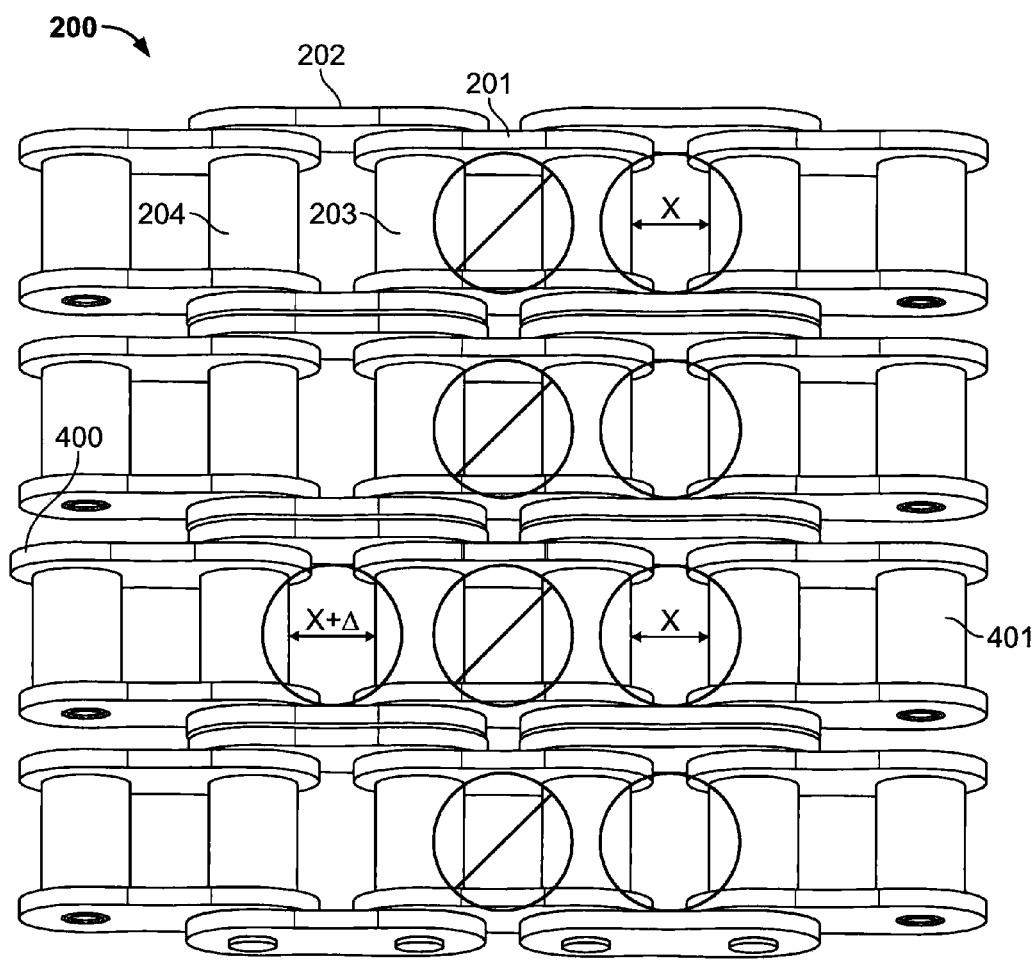
FIG. 4 is a top view of the multistand roller chain of FIG. 2 illustrating where the chain is measured using the roller chain wear gauge of FIG. 1 according to an embodiment of the present disclosure.

FIG. 4 is a top view of the multistand roller chain of FIG. 2 illustrating where the chain is measured using the roller chain wear gauge of FIG. 1 according to an embodiment of the present disclosure. What is shown with a circle having a diagonal bar in the center portion of the roller chain 200. Sections of the chain that must not be tested between two rollers 203 are located on the same internal link. What is shown with a circle corresponds to the numerous positions where the wear gauge 100 must be inserted in the roller chain 200 to fully test the roller chain 200. The unworn distance is shown as X on FIG. 4 and the worn distance is shown as X+Δ where the symbol Δ (delta factor) represents the small variation increment associated with a worn link. In one embodiment, the delta factor is at least 3% of the size of the opening of the chain (e.g., the pitch) without wear for an adjustable drive roller chain and at least 1.5% of the size of the opening of the chain without wear for a fixed-center drive roller chain. In one embodiment, the measuring end 2 includes eight calibrated segments 6A-H and the width of the calibrated segment for chain #200 and #264 is equal and shown in 6B. In yet another embodiment, when a chain reaches a delta factor of 3% the chain may start skipping over the different teeth on a sprocket. Damages may occur at lower delta factors such as for example 1.5%.

Illustrated as 400 on FIG. 4 is the situation where part of the roller chain 200 is worn out. The inner distance between the external surface of the bushings 203, 204, which is initially X, becomes X+Δ. The gauge 100 is then slid into position as illustrated in FIG. 5. In the case where the roller chain is of size ANSI #100, the interstice X+Δ allows the section 6F to slide between the pins 205 distant by the worn pitch Y+Δ until the marking 12 is hidden behind the external plate 202. What is shown in FIG. 1 is a gauge 100 where a rail 5 allows the tool to slide without damaging the different rollers or bushings 203 of a roller chain 200 as shown in FIG. 2. What is also contemplated is the use of a stop 7 or a plurality of stops or guides placed alongside the measuring end 2 to facilitate the insertion of the gauge 100 within the roller chain 200 for taking measurements.

Figure 6:
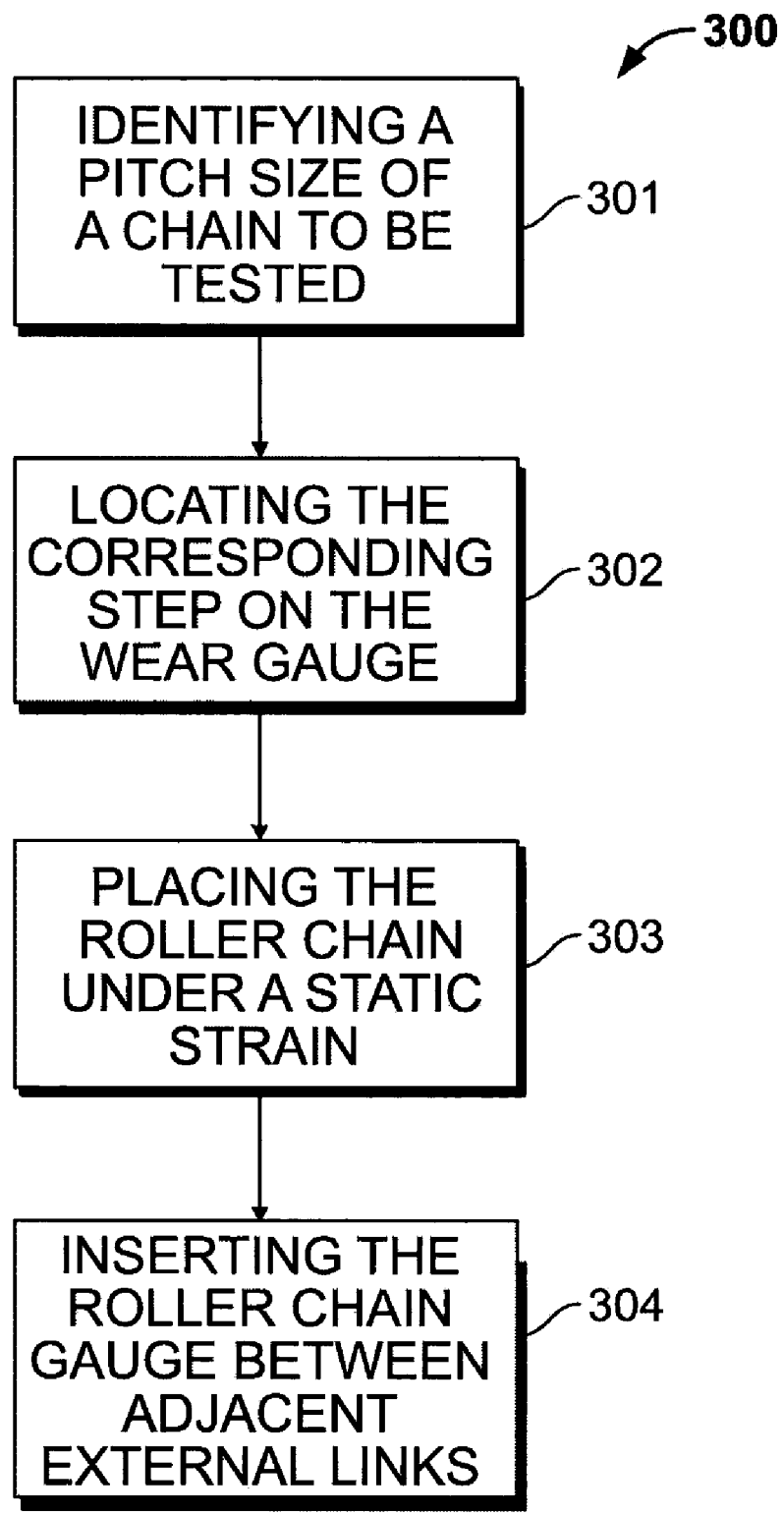
FIG. 6 is a block diagram of a method for measuring the wear of a roller chain using the roller chain wear gauge of FIG. 1 according to a possible embodiment of the present disclosure.

FIG. 6 is a block diagram of a method for measuring the wear of a roller chain using the roller chain wear gauge. The method for measuring the wear of a roller chain 300 includes the successive steps of identifying 301 a pitch size P of a chain 100 to be tested, locating 302 the corresponding step 6A-G on a roller chain wear gauge 100 as described above, placing 303 the roller chain 200 under a static strain, and inserting 304 successively the roller chain wear gauge 100 between adjacent external links.

Persons of ordinary skill in the art appreciate that although the teachings of the disclosure have been illustrated in connection with certain embodiments and methods, there is no intent to limit the invention to such embodiments and methods. On the contrary, the intention of this disclosure is to cover all modifications and embodiments failing fairly within the scope the teachings of the disclosure.

What is claimed is:

1. A roller chain wear gauge, comprising:
    a single-piece body with a measuring end and a handle connected to the measuring end,
    wherein the measuring end includes a plurality of adjacent and contiguous calibrated segments for insertion between adjacent external links in a link of the roller chain each calibrated segment having a different measuring length, a fixed measuring width over the measuring length, and a measurement marking, and wherein the measuring end defines on one side a back rail formed by an alignment of a first side of each of the calibrated segments and a step function formed by the second side of each of the calibrated segments.

2. The roller chain wear gauge of claim 1, wherein the measurement marking on each of the calibrated segments is a size of the chain to be gauged by the marked segment.

3. The roller chain wear gauge of claim 2, wherein the measuring width of each of the calibrated segments is the size of an opening of the chain to be gauged by the marked segment without wear plus a wear delta factor.

4. The roller chain wear gauge of claim 3, wherein the delta factor is at least 300 of the size of the opening of the chain without wear for an adjustable drive roller chain.

5. The roller chain wear gauge of claim 3, wherein the delta factor is at least 1.5% of the size of the opening of the chain without wear for a fixed-center drive roller chain.

6. The roller chain wear gauge of claim 1, wherein the measuring end includes eight calibrated segments with measure marking of 240, 200/264, 160, 180, 140, 120, 100, and 80, respectively.

7. The roller chain wear gauge of claim 6, wherein the widths of the calibrated segments 200 and 264 are equal.

8. The roller chain wear gauge of claim 1, wherein the measuring end includes seven calibrated segments with measure marking of 24, 20, 16, 12, 10, 08, and 06, respectively.

9. The roller chain wear gauge of claim 1, wherein the measuring end includes six calibrated segments with measure marking of 100, 80, 60, 50, 40, and 35, respectively.

10. A method for measuring the wear of a roller chain, the method comprising the steps of:
    identifying a pitch size of a chain to be tested;
    locating the corresponding step on a roller chain wear gauge comprising a single-piece body with a measuring end and a handle connected to the measuring end, wherein the measuring end includes a plurality of adjacent and contiguous calibrated segments for insertion between adjacent external links in a link of the roller chain each calibrated segment having a different measuring length, a fixed measuring width over the measuring length, and a measurement marking, and wherein the measuring end defines on one side a back rail formed by an alignment of a first side of each of the calibrated segments;
    placing the roller chain under static strain; and
    inserting successively the roller chain wear gauge between adjacent external links.

* * * * *

UNITED STATES PATENT AND TRADEMARK OFFICE
CERTIFICATE OF CORRECTION

| | | |
|---|---|---|
| PATENT NO. | : 7,654,149 B2 | Page 1 of 1 |
| APPLICATION NO. | : 12/025553 | |
| DATED | : February 2, 2010 | |
| INVENTOR(S) | : Wilbur | |

It is certified that error appears in the above-identified patent and that said Letters Patent is hereby corrected as shown below:

Col. 6, line 19; delete "300" and replace with "3%".

Signed and Sealed this

Thirteenth Day of April, 2010

David J. Kappos
*Director of the United States Patent and Trademark Office*